United States Patent [19]

Schroeder et al.

[11] Patent Number: 5,647,053
[45] Date of Patent: Jul. 8, 1997

[54] VAPOR DIPENSING DEVICE

[75] Inventors: John A. Schroeder, Mt. Pleasant; Armin L. Clobes, Wind Point; Mark E. Wefler, Mt. Pleasant, all of Wis.; Terry L. Hygema; Kevin W. Smith, both of North Webster, Ind.

[73] Assignee: S. C. Johnson & Son, Inc., Racine, Wis.

[21] Appl. No.: 541,050

[22] Filed: Oct. 11, 1995

[51] Int. Cl.⁶ .................................. F24F 6/00; F24F 6/08
[52] U.S. Cl. ........................ 392/390; 392/395; 122/242
[58] Field of Search .......................... 392/392, 394, 392/395, 390; 122/242, 243, 366; 239/44; 261/97, 99

[56] References Cited

U.S. PATENT DOCUMENTS

| | | | |
|---|---|---|---|
| 3,872,280 | 3/1975 | Van Dalen | 392/392 |
| 4,467,177 | 8/1984 | Zobele | 392/392 |
| 5,038,394 | 8/1991 | Hasegawa et al. | 392/395 |
| 5,095,647 | 3/1992 | Zobele | 392/392 |
| 5,222,186 | 6/1993 | Schimanski et al. | 392/395 |
| 5,290,546 | 3/1994 | Hasegawa | 392/395 |

*Primary Examiner*—Teresa J. Walberg
*Assistant Examiner*—Sam Paik

[57] ABSTRACT

A vapor dispensing device having an outer shell (10); a one piece electric plug heater block (40) having attached electric plug pins (48), the block being attached to the outer shell such that the block can rotate a predetermined amount around an axis parallel to the plug pins; and a wick (36) in fluid communication with a material to be dispensed and extending into an opening (52) through the block; wherein the opening has a shape defined by the rotation through an internal angle at least equal to the predetermined amount of rotation of a solid geometric shape transverse to the axis and wherein the block has an electric heating element (60) in close proximity to the opening.

4 Claims, 5 Drawing Sheets

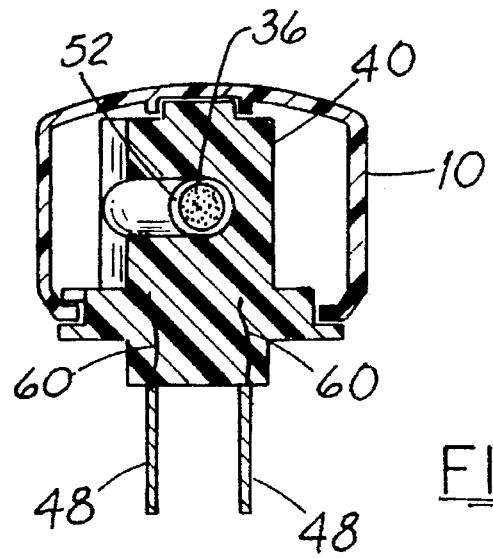
FIG. 4
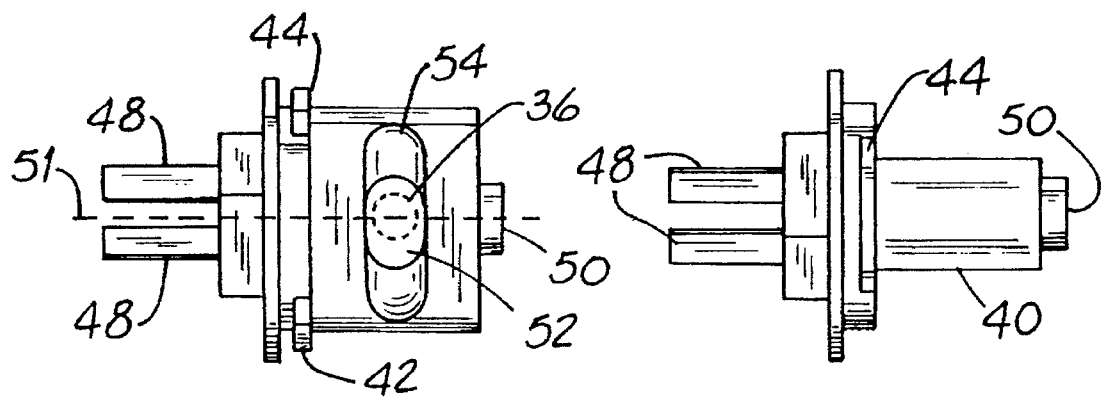
FIG. 5  FIG. 6
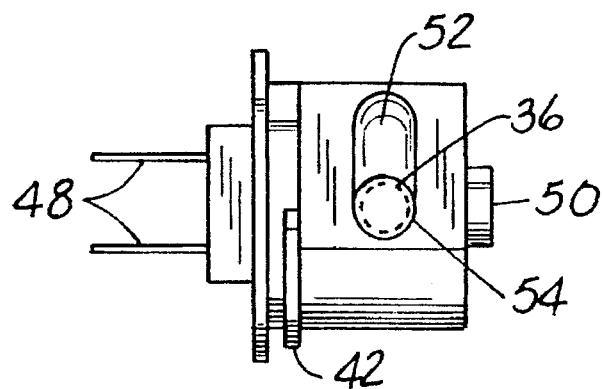 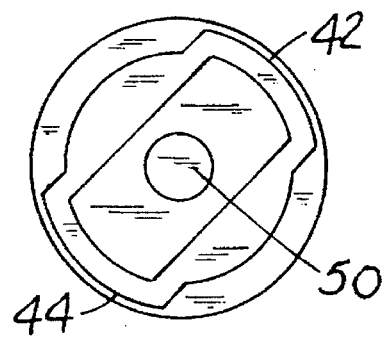
FIG. 7  FIG. 8

VAPOR DIPENSING DEVICE

TECHNICAL FIELD

This invention relates to devices to vaporize materials and particularly liquids into the atmosphere. More particularly, this invention relates to an improved plug and heater block assembly for use in devices to vaporize a material drawn up by a wick.

BACKGROUND ART

In the past, liquid vaporizers which use a wick and a heating device have either had fixed electric plug pins as disclosed in U.S. Pat. No. 4,467,177 or had electric pins which rotate relative to the shell connected by wires to a fixed heater element as disclosed in U.S. Pat. Nos. 5,290,546 and 5,095,647. The reason for using rotating plug pins is that it is important for the proper functioning of the wick that the wick be essentially perpendicular to the ground. However, depending on the way the electric plug outlet is installed, the orientation of the plug pins can vary by 90 degrees.

DISCLOSURE OF INVENTION

The present invention is directed to a vapor dispensing device which comprises: (a) an outer shell; (b) a one piece electric plug heater block having attached electric plug pins, the block being rotably attached to the outer shell such that the block can rotate through a predefined range of rotation around an axis parallel to the plug pins; and (c) a wick in fluid communication with a material to be dispersed and extending into an opening through the block; wherein the opening has a shape defined by the rotation of a solid geometric shape transverse to the axis through an internal angle at least equal to the predefined rotation of the block and wherein the block has an electric heating element in close proximity to the opening.

BRIEF DESCRIPTION OF THE DRAWINGS

FIG. 4 is a view taken along line 4—4 in FIG. 3a.

FIG. 5 is a view of the plug heater block alone with the plug pins at a 45 degree angle.

FIG. 6 is a view of the plug heater block alone taken 90degrees relative to FIG. 5.

FIG. 7 is a view of the plug heater block alone taken 45degrees relative to FIG. 5.

FIG. 8 is an end view of the plug heater block of FIG. 5.

MODES FOR CARRYING OUT THE INVENTION

Figure 1:
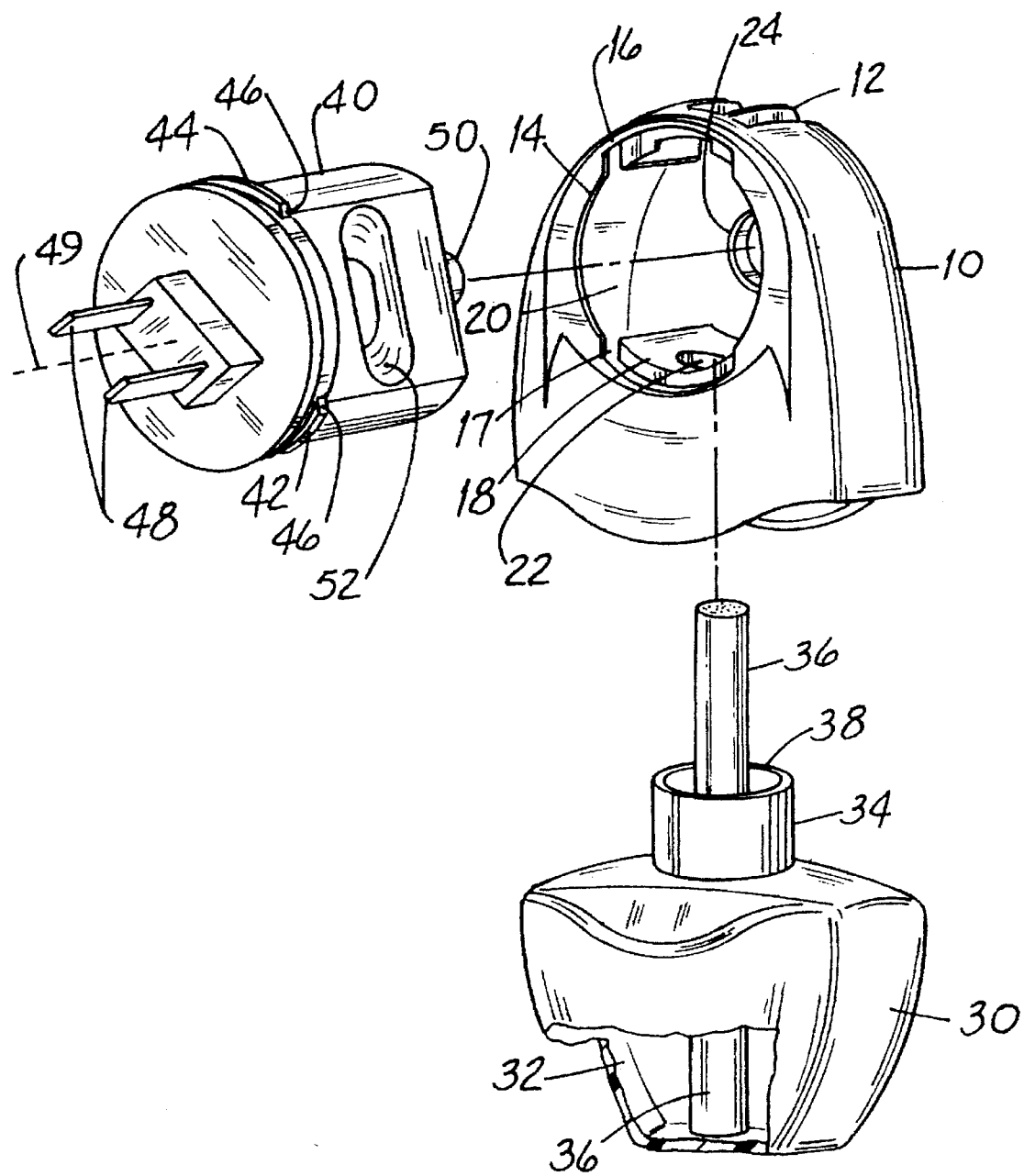
FIG. 1 is a three quarter exploded view of the vapor dispensing device with a section of the container partially broken away.
Figure 2:
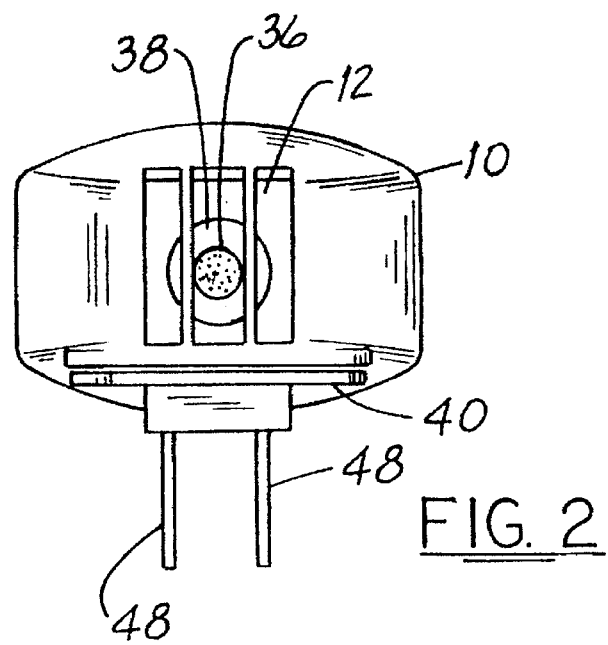
FIG. 2 is top view of the vapor dispensing device.
Figure 10:
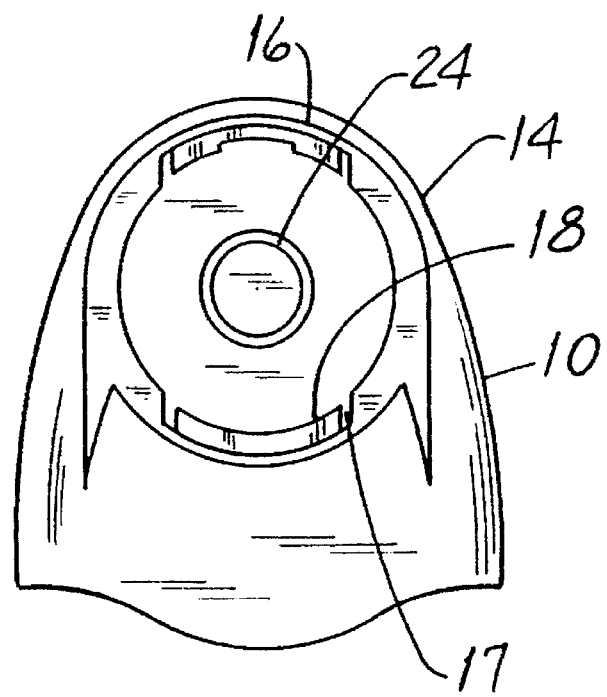
FIG. 10 is a view of the shell with the block removed.

As shown in FIG. 1, the vapor dispensing device includes an outer shell 10 having vapor dispensing opening 12. As seen in FIGS. 1 and 10, shell 10 has a generally circular opening 14. Opening 14 has two cutouts 16 and 17 which cooperate with flanges 42 and 44 to enable plug heater block 40 to be held in place in shell 10. As plug heater block 40 is inserted into opening 14, block 40 is held in place by deformable tabs (not shown) or by any other conventional attaching means that enables block 40 to partially rotate within opening 14, as will be described later, but not be removed once inserted. Also visible in FIG. 1 are container attaching means 18, air flow opening 20, a second similar opening on the other side of attaching means 18, not shown, and wick opening 22. The function of each of these elements is well known to those of skill in the art and will not be repeated here.

Container 30 is a conventional bottle or similar device well known to those skilled in the art and is sealed with closure 38, which holds wick 36 firmly in place. Generally closure 38 is not easily removable and also generally and preferable cooperates with wick 36 so that wick 36 is not easily removable from container 30. Within container 30 is a liquid 32, which is the material to be volatilized. Material 32 can be any of a number of conventional materials dispensed from this type of vapor dispenser, including fragrances, disinfectants, sanitizing agents, insect repellents, insecticides and the like. Container 30 has a container neck 34 which cooperates in a known fashion with container attaching means 18 to hold container 30 and wick 36 firmly in place. Preferably, attaching means 18 will enable the user of these devices to change the container when liquid 32 is exhausted. Suitable means include bayonet attachments, undercuts with matching projections, and the like.

Figure 11:
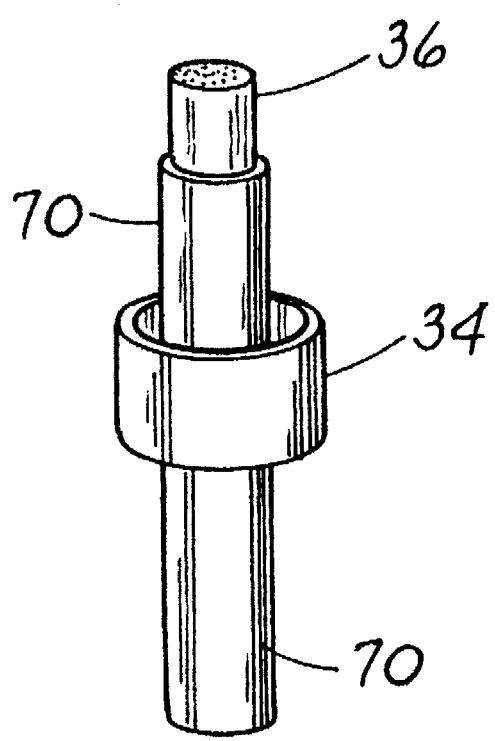
FIG. 11 is a ¾ view of an alternative embodiment of the wick.

As an alternative embodiment as shown in FIG. 11, wick 36 can be enclosed in a sheath 70. Neck 34 or other suitable attaching methods can be attached to sheath 70 to hold wick 36 in place in the unit. Sheath 70 is closed at the bottom end and acts as a container for the material to be dispensed by the unit.

As shown in FIG. 1 and more clearly in FIG. 10, shell 10 includes a rotation guide detent 24 in the front wall of shell 10. Detent 24 cooperates with rotation guide projection 50 on block 40 to support the far end of block 40 when it is inserted into shell 10.

When container 30 is inserted into the bottom of shell 10 as shown in FIG. 3, the top of wick 36 passes through wick opening 22 and into block opening 52. Typically the top of wick 36 will extend to about top edge 54 of block opening 52. This will enable the heat generated by the heating element, as described herein, to be near the top of wick 36. This either vaporizes liquid 32 or forms small aerosol sized particles of liquid 32 which has been drawn up wick 36 through vapor dispensing opening 12 to the atmosphere. As used herein, the term "vaporize" is intended to also include the formation of very small aerosol sized particles which can remain suspended for extended periods of time in the air as well as the formation of actual vapors.

Figures 3A, 3B:
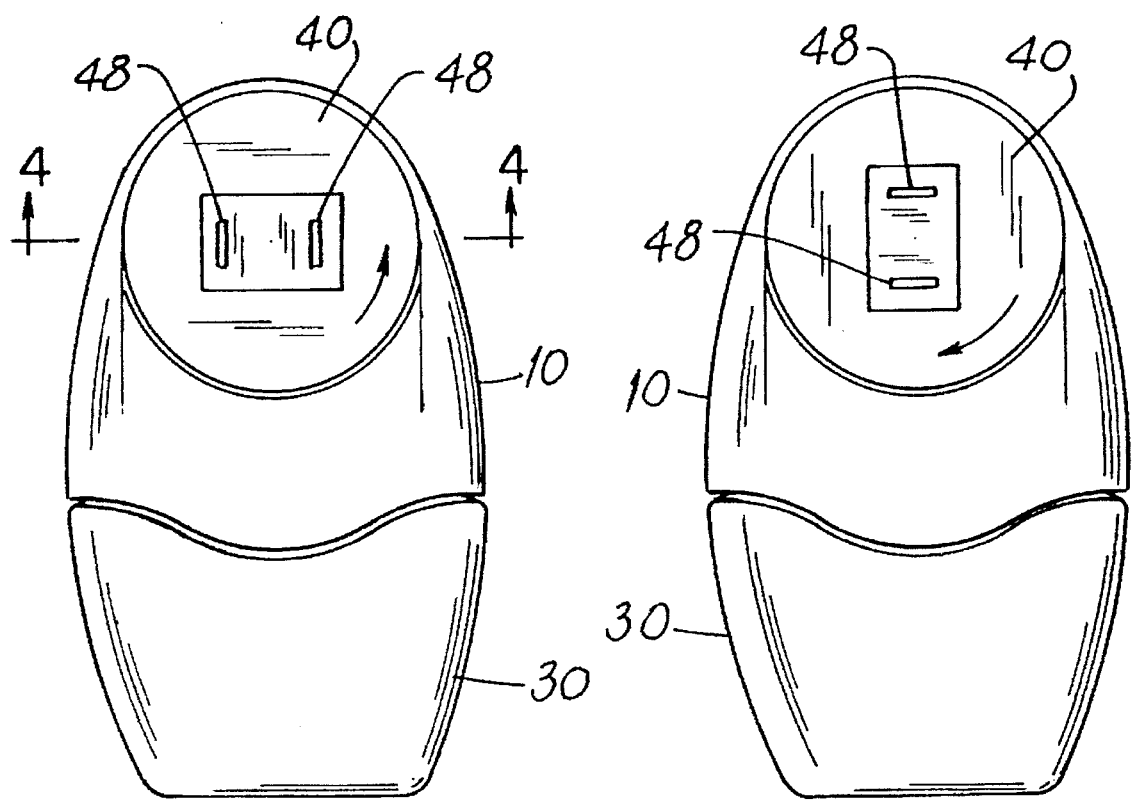
FIG. 3a is a back view of the vapor dispensing device
FIG. 3b is a back view of the vapor dispensing device with the plug heater block rotated 90 degrees.

As shown in FIGS. 3a and 3b, block 40 can be rotated approximately 90 degrees around axis 49 (FIG. 1) parallel to plug pins 48 and extending through the center of rotation guide projection 50 to enable the unit to be plugged into a conventional electric outlet so that wick 36 is approximately perpendicular to the ground.

Shell 10 can be made from any material capable of being molded. Since the unit includes a heating element, the plastic materials chosen should not deform under the operating temperatures and conditions of the unit. Suitable materials include thermoplastic or thermoset polymers such as polypropylene, polyphenolsulfide or polyvinylchloride.

Figure 9:
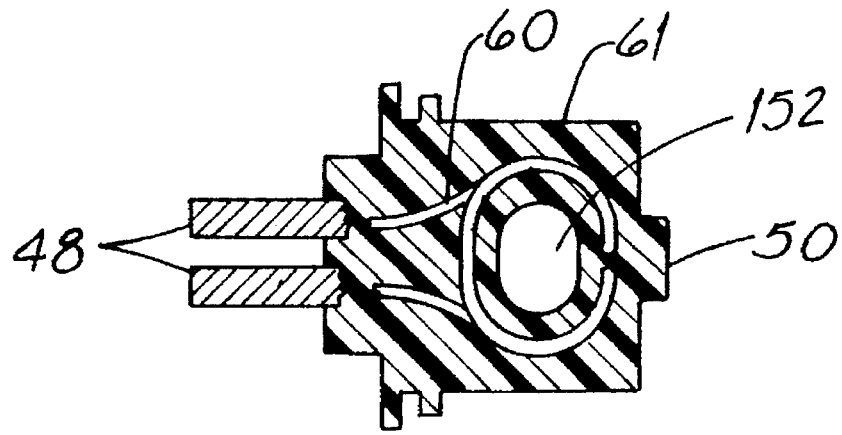
FIG. 9 is a top view of the premolded insert part.

FIG. 4 shows the relation of block 40, shell 10 and wick 36. Opening 52 surrounds wick 36 and is in close proximity to wick 36. Heating element 60 is just below the surface of opening 52 as shown in FIG. 9. While the type of heating element as shown in the attached figures is a heating wire, any type of conventional heating element can be used so long as the heating element can be included within a molded element. Other suitable heating elements include positive temperature co-efficient heaters and other similar conventional elements.

Block 40 is formed by forming a premolded unit 61, shown in FIG. 9, which includes heating element 60 which surrounds opening 152. Heating element 60 is electrically connected to plug pins 48 which are also included in premolded unit 61. Premolded unit 61 is then overmolded using conventional techniques to form the shape as shown in FIGS. 5, 6, 7 and 8. Opening 152 should be large enough so that opening 52 can be easily molded.

Opening 52 is molded into a shape which accommodates wick 36 and enables block 40 to be rotated any desired or predefined degree of rotation. It is preferred that this degree of rotation be approximately 90 degrees. The shape of opening 52 is defined by the rotation of a three dimensional geometric shape, such as a cylinder, cube, 3D triangles, and the like through an internal angle equal to the predefined degree of rotation transverse to axis 49. While any shape can be used, geometric shapes with a circular cross-section are preferred since these enable opening 52 to minimize the air space between the surface of block 40 and wick 36.

Block 40 can be formed from any materials that are both electrically insulating and resistant to deformation at the temperatures at which the unit will be operated. Premolded unit 61 and block 40 can be formed from the same or different materials depending on the application. For most applications block 40 and premolded unit 61 will be formed from the same moldable materials. Suitable materials include thermoplastic or thermoset polymers such as polypropylene, polyphenolsulfide or polyvinylchloride.

Wick 36 can be formed from any conventional wick materials. Suitable wick materials include porous/sintered plastics such as ultra high density polyethylene and polypropylene; bonded fibers such as polyesters and polypropylene; glass-sintered fibers; porous ceramic, carbon fiber; sintered carbon; wood, compressed wood composites, bundled or woven natural fibers such as cotton, wood, linen, bundled or woven man made fibers such as nylon, polypropylene, polyethylene, polyesters, polyamides, rayon, polyacetates, etc. Because the spacing of opening 52 is such that the heating element will not surround the entire wick near its top, it is preferred to use a wick that has an impermeable sheath as described in an application filed in the name of John A. Schroeder and Armin L. Clobes on the same day as the present invention Ser. No. 08/541,051 filed Oct. 11, 1995. While the use of this sheathed wick is not necessary, for some materials to be dispensed, the wrapped wick provides improved performance.

Industrial Applicability

The use of a single piece plug heater block 40, makes the assembly of these type of vapor dispensing units easier and more cost efficient than the multipart assemblies as disclosed in the prior art. In addition, since there are no moving parts, there is less opportunity for a unit to become non-functional because a part broke or became disconnected in use. Also, block 70 allows the plug to be rotated without removing wick 36.

We claim:

1. A vapor dispensing device which comprises:
   (a) an outer shell;
   (b) a one piece electric plug heater block having attached electric plug pins, the block being rotatably attached to the outer shell such that the block can rotate through predefined range of rotation around an axis parallel to the plug pins; and
   (c) a wick in fluid communication with a material to be dispensed and extending into an opening through the block;

wherein the opening has a shape defined by rotating a solid geometric shape transverse to the axis through an angle at least equal to the predefined range of rotation of the block and wherein the block has an electric heating element in close proximity to the opening.

2. The device of claim 1 which further includes a container attached to the shell which contains the material to be dispensed.

3. The device of claim 1 wherein the geometric shape is a cylinder.

4. The device of claim 1 wherein the range of rotation is about 90 degrees.

* * * * *